US009157056B2

(12) United States Patent
Eggersmann

(10) Patent No.: US 9,157,056 B2
(45) Date of Patent: Oct. 13, 2015

(54) DEVICE AND METHOD FOR RECOVERING BIOGAS

(75) Inventor: Karlgünter Eggersmann, Marienfeld (DE)

(73) Assignee: Zero Waste Energy, LLC, Lafayette, CA (US)

( * ) Notice: Subject to any disclaimer, the term of this patent is extended or adjusted under 35 U.S.C. 154(b) by 436 days.

(21) Appl. No.: 13/383,723

(22) PCT Filed: Jun. 17, 2010

(86) PCT No.: PCT/EP2010/003668
§ 371 (c)(1),
(2), (4) Date: Jan. 12, 2012

(87) PCT Pub. No.: WO2011/006570
PCT Pub. Date: Jan. 20, 2011

(65) Prior Publication Data
US 2012/0115185 A1    May 10, 2012

(30) Foreign Application Priority Data

Jul. 13, 2009  (EP) ...................................... 09009128
Sep. 18, 2009  (EP) ...................................... 09011906

(51) Int. Cl.
*A61L 9/01* (2006.01)
*C12P 1/00* (2006.01)
(Continued)

(52) U.S. Cl.
CPC ............... *C12M 21/04* (2013.01); *C12M 23/50* (2013.01); *C12M 23/58* (2013.01); *C12M 29/02* (2013.01); *C12M 37/00* (2013.01); *C12M 41/18* (2013.01); *Y02E 50/343* (2013.01)

(58) Field of Classification Search
CPC ...... C12M 21/04; C12M 27/02; C12M 29/04;
C12M 29/18; C12M 41/32; Y02E 50/343;
C02F 2209/005; C02F 3/06; C02F 3/1215;
C02F 3/2806; C02F 3/30; C02F 3/308;
C05F 17/0018; C12P 5/023; Y10S 210/903
See application file for complete search history.

(56) References Cited

U.S. PATENT DOCUMENTS 5,269,634 A     12/1993  Chynoweth
2004/0237859 A1 * 12/2004 Hartmann ...................... 110/341
(Continued)

FOREIGN PATENT DOCUMENTS

CA     2337568 A1 *  8/2002
DE     19719323       11/1998
(Continued)

OTHER PUBLICATIONS

English Translation of DE102006009165.*
(Continued)

*Primary Examiner* — Chris R Tate
*Assistant Examiner* — Douglas F White

(57) ABSTRACT

A device for recovering biogas, comprising at least one fermenter (13) and a percolate tank (10) for collecting the percolate removed from the fermenter or fermenters (13). The percolate tank (10) has a percolate inlet (10c) that can be connected to an outlet of the fermenter or fermenters (13) and a percolate outlet (10b). The percolate tank (10) is designed in such a way that the residence time of the percolate as it passes between the inlet (10c) and the outlet (10b) is sufficiently long to sanitize the percolate at the outlet (10b). The Percolate tank may also include one or more heaters to heat the percolate.

8 Claims, 3 Drawing Sheets

(51) Int. Cl.
*C12M 1/36* (2006.01)
*C12M 1/38* (2006.01)
*C12M 3/00* (2006.01)
*C12M 1/107* (2006.01)
*C12M 1/00* (2006.01)
*C12M 1/12* (2006.01)
*C12M 1/02* (2006.01)

(56) References Cited

U.S. PATENT DOCUMENTS

2008/0028675 A1* 2/2008 Clifford et al. ............... 44/605
2009/0068725 A1* 3/2009 Lutz ........................ 435/286.5

FOREIGN PATENT DOCUMENTS

| | | |
|---|---|---|
| DE | 29902143 | 5/1999 |
| DE | 102005037452 | 8/2006 |
| DE | 102006009165 | 1/2007 |
| DE | 202006002757 | 6/2007 |
| EP | 1428868 | 6/2004 |
| EP | 1736535 | 12/2006 |
| WO | WO 0206439 | 1/2002 |

OTHER PUBLICATIONS

International Search Report and Written Opinion for PCT/EP2010/003668, Dec. 28, 2010, German Intellectual Property Office.
International Preliminary Report on Patentability for PCT Application PCT/EP2010/003668, WIPO, Jan. 17, 2012.

* cited by examiner

US 9,157,056 B2

DEVICE AND METHOD FOR RECOVERING BIOGAS

TECHNICAL FIELD

The invention relates to a device and a method for recovering biogas and more particularly, to a system and method wherein a percolate tank, connected to one or more fermenters, is designed in such a way that the residence time of the percolate as it passes between the inlet and the outlet of the percolate tank is sufficiently long to sanitize the percolate at the outlet.

BACKGROUND INFORMATION

During the methanization of biomass, fermenters are used in which a fermentation process runs, wherein methane-containing gas is produced by the fermentation of the biomass. A distinction is made between the so-called continuous process and the discontinuous process (batch process). In the latter, a percolate containing microorganisms is introduced into a fermenter, which percolates through the substrate (biomass) and is collected in a percolate container and is re-introduced into the fermenter, if necessary, until the biomass contained in the fermenter has been fermented. The fermented biomass is subsequently removed from the fermenter and must be purified, if necessary, and be utilized in the customary manner. To facilitate the recovery, it may be necessary that the fermented biomass is sanitized. This means that the biomass must be free of undesirable germs, bacteria, or other impurities, so that the fermentation residue can be recovered. The same is also applicable for the percolate which likewise contains corresponding bacteria and the like and must likewise be sanitized so as not to re-infect the already sanitized biomass in the fermenter during recycling.

SUMMARY

The object of the present invention therefore is to provide a device and a method of the type mentioned at the outset, with which a fermentation plant can be operated discontinuously without re-infecting the biomass in the fermenter.

The invention teaches that the residence time of the percolate in the percolate tank is arranged such that the percolate is sanitized at the percolate outlet of the percolate tank. For sanitization, the percolate is preferably heated in a heating section downstream of the percolate inlet of the percolate tank to a thermophilic temperature range of typically between 48° C. and 60° C., preferably above 50° C. (other temperatures, even below 50° C. are also possible, depending on the circumstances and the microorganisms used) and is routed through the percolate. For this purpose it is preferably provided that the flow path is designed so that it meanders between the percolate inlet and the percolate outlet, facilitating a particularly long residence time in the percolate tank as a result of the extended distance at a temperature that is adjusted in the thermophilic range to ensure that only sanitized percolate can exclusively be removed at the percolate outlet, which during the percolation through the fermenter can no longer re-infect the biomass present there.

According to a preferred embodiment, two sand traps are used, one of which is exclusively supplied with sanitized percolate and one with non-sanitized percolate. The feed from the fermenters used depends on whether the fermenter provides sanitized or non-sanitized percolate at its outlet. The percolate that is in the sand trap for non-sanitized percolate is then supplied into the percolate tank, where it is sanitized. The percolate that is in the sand trap for sanitized percolate can likewise overflow into the percolate tank and also enters the percolate outlet in the sanitized state. In this context it is especially advantageous to operate at least one fermenter in the thermophilic range, since the sanitization is then accomplished.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

The following description of the preferred embodiment refers to all Figures equally.

Figure 1A:
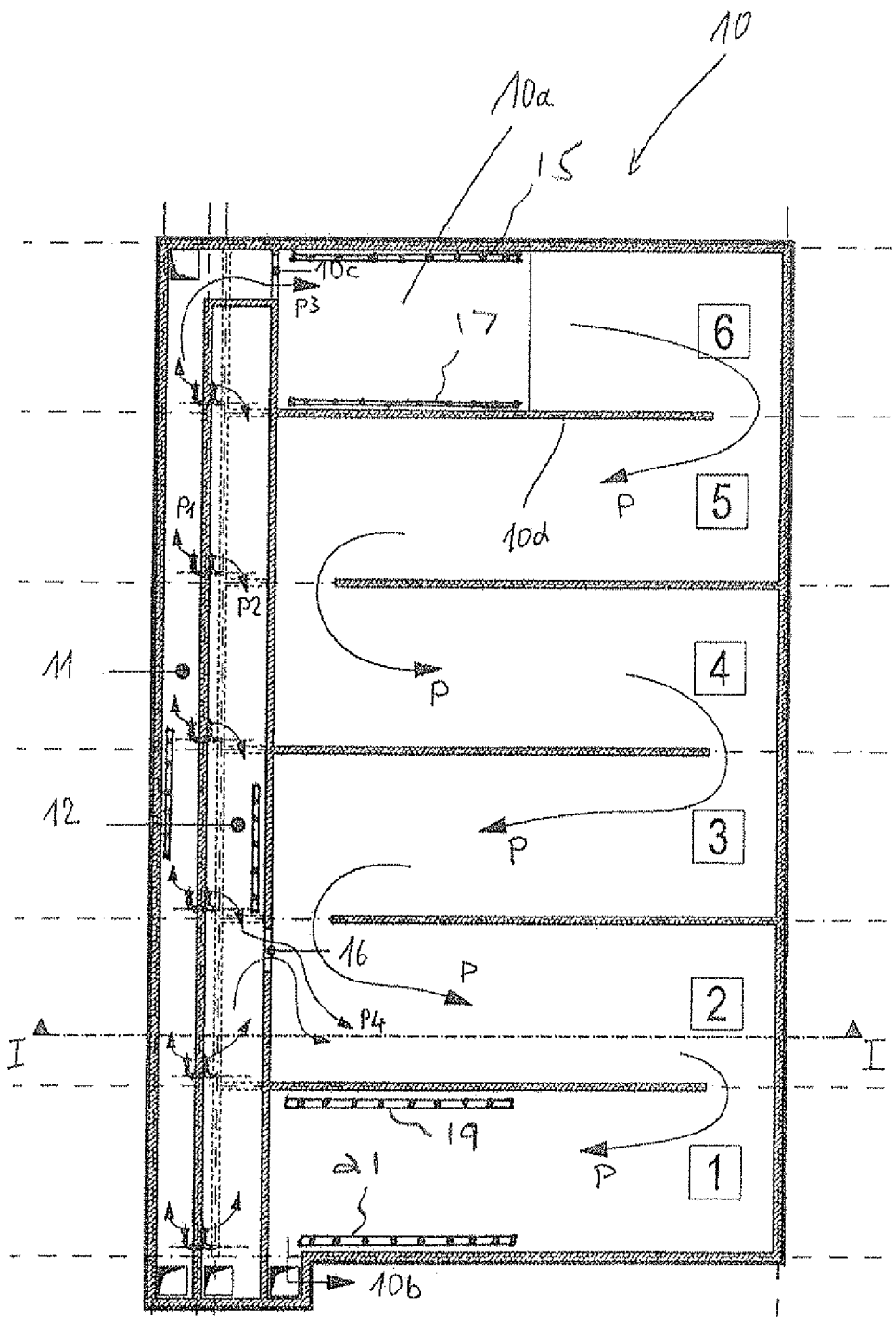
FIG. 1A—shows a part of a preferred embodiment for the device as taught by the invention as a horizontal projection incorporating internal heaters.
Figure 1B:
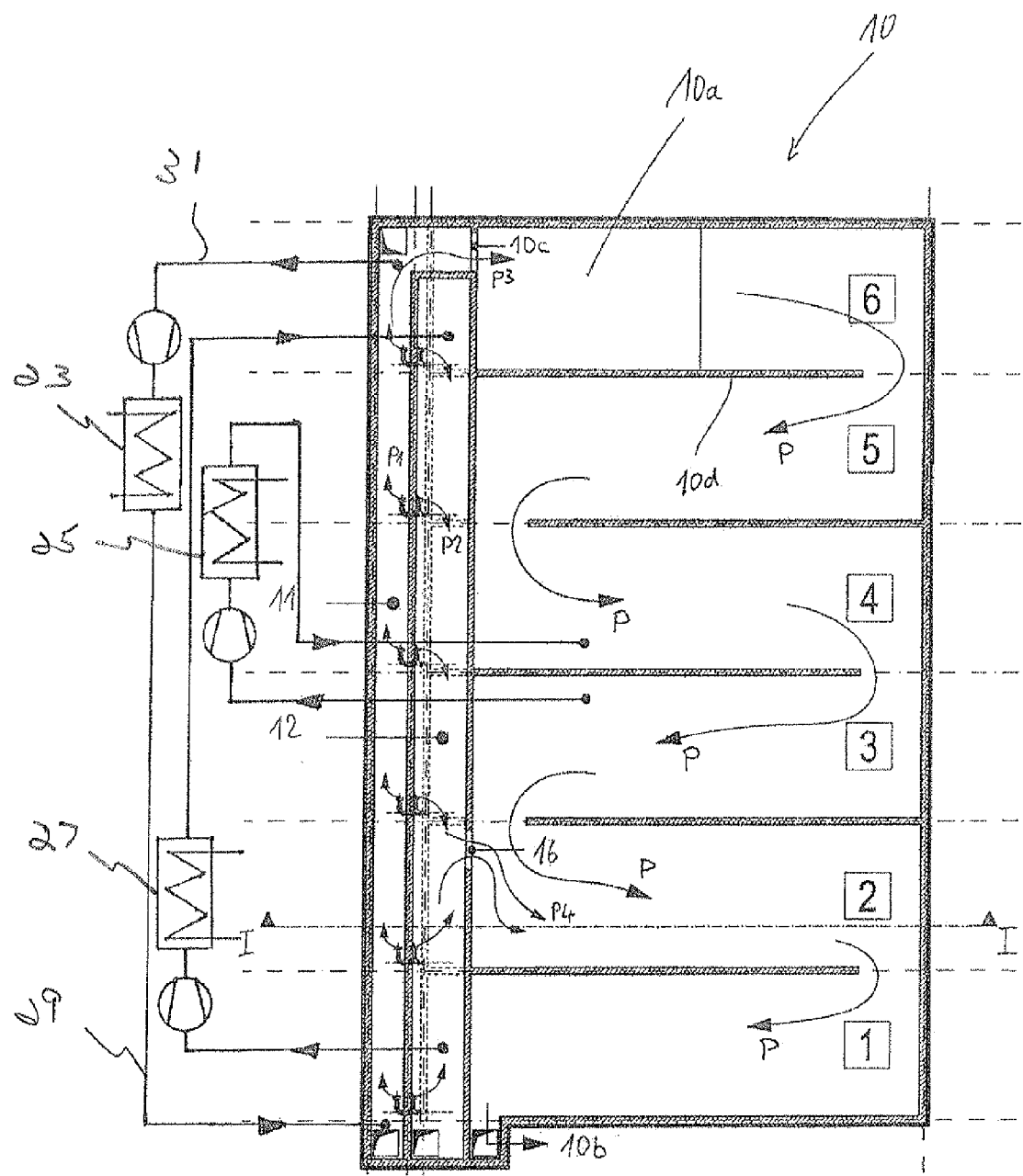
FIG. 1B—shows a part of another embodiment for the device as taught by the invention as a horizontal projection incorporating external heaters.
Figure 2:
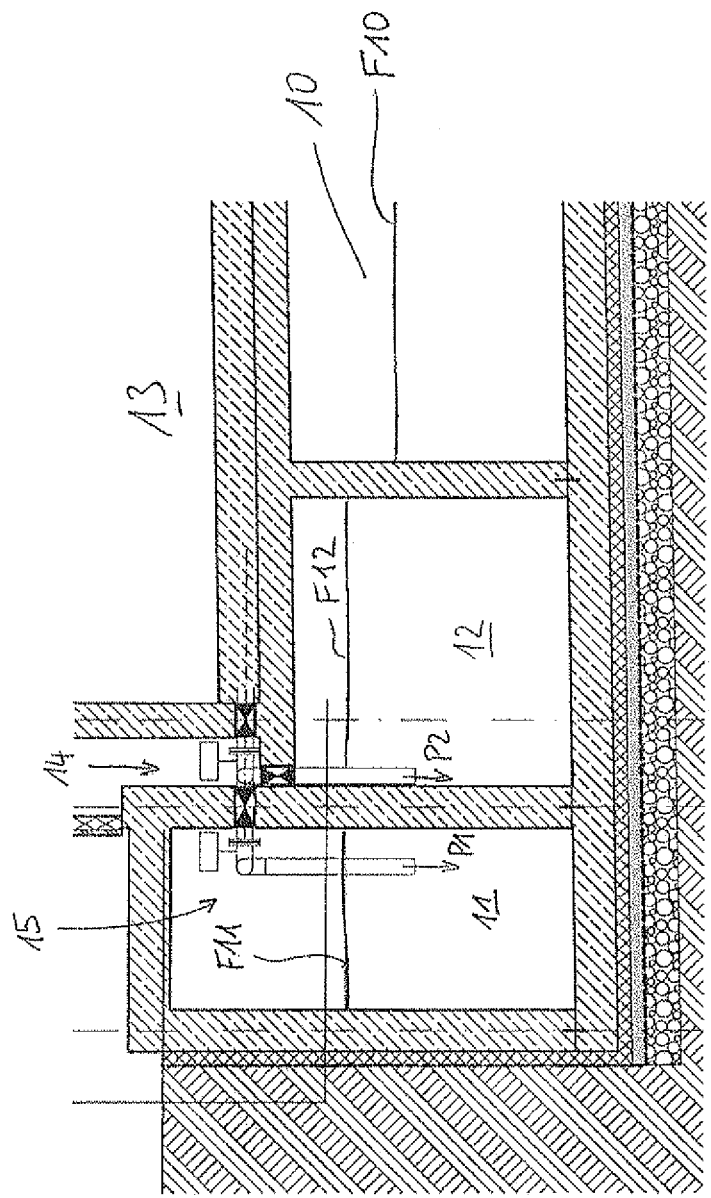
FIG. 2—shows a cross-section through the device along a line I-I in FIG. 1.

The illustrated device preferably has a two-story design. In the upper story (not shown in FIGS. 1A and 1B), one or a plurality of fermenters 13 (see FIG. 2) are located into which a substrate of biomass to be fermented is introduced. In the level lying below the fermenters 13, a plan view of which is represented in FIGS. 1A and 1B, a percolate tank 10 is located which preferably has a plurality of chambers 1-6, which in the embodiment shown are separated from each other by means of walls 10d, wherein the standing baffles 10 do not have a continuous design but make it possible for the percolate to flow from one chamber (e.g. 6) into the respective adjacent chamber (e.g. 5). The walls 10d are preferably arranged such that a meandering flow path for the percolate results from the percolate inlet 10c in chamber 6 to the percolate outlet 10b in chamber 1, which is indicated by the arrows P. Other forms of flow paths are also conceivable, which have a spiral or helical shape, for example.

In the example shown, this level furthermore has two apparatuses that are designed as sand traps for cleaning the percolate 11 and 12. This shows a sand trap for sanitized percolate 12 (subsequently called "sand trap 'white'") and a sand trap for non-sanitized percolate 11, subsequently called "sand trap 'black.'") As particularly shown in FIG. 2, any percolate removed from the fermenters 13 can be fed into the sand trap 'black' 12 (path P2) or into the sand trap 'white' (path P2) via a valve system 14, 15. From the sand trap 'white' 12, the percolate can flow through an opening or a standing baffle 16, which is designed high enough so that sanitized percolate from the sand trap 'white' can enter into a chamber 2 of the percolate tank 10 in the direction of the arrow P4, yet any backflow from the chamber 2 into the sand trap 'white' 12 is not possible. For this purpose, the filling level F10 of the percolate in the percolate tank 10 is kept below the opening or the baffle wall 16 and/or below the filling level F12 in the sand trap 'white.'

From the sand trap 'black' 11, the percolate reaches the percolate tank 10 via a percolate inlet 10c, which can be designed as an opening or as a standing baffle, and then enters into the chamber 6. Same as above, the filling level F11 in the sand trap 'black' and/or the percolate inlet 10c is also located above the filling level F10 in the percolate tank 10.

The plant now operates such that in each case percolate, which, in the first embodiment shown in FIG. 1A, enters chamber 6 of the percolate tank 10 (path P3) through the inlet 10c, is initially heated by heaters 15/17 (herein shown located in the first section 10a facing the inlet 10c although this is not a limitation of the present invention) in a heating section. For this purpose, the temperature of the percolate is preferably heated to a temperature in the thermophilic range of generally between 48° C. and 60° C., whereafter it is routed in a meandering path (as illustrated by arrows P) through the individual chambers 6 through 1.

The path length P and the temperature of the percolate are adjusted such that exclusively sanitized percolate can be removed from the percolate outlet 10b in chamber 1, which can then be returned into the fermenters 13, if necessary. One or more additional heaters in one or more chambers may be provided such as for example heaters 19/21 in chamber 1. Alternatively, one or more heaters 23/25/27 may be provided outside the chambers 6-1 by providing one or more paths for example 29/31 through which the percolate may flow and be heated before returning the percolate to a chamber or sand trap as illustrated in the embodiment shown in FIG. 1B.

By returning the "warm" percolate at a temperature in a range of preferably above 50° C. into the fermenter 13, the substrate (biomass) which exists there is also gradually brought up to temperature until it also has a temperature in the thermophilic range after a certain period of time (a few days), same as the percolate in the percolate tank. By the then thermophilic operation of the respective fermenter, the biomass contained therein will also be sanitized, so that only sanitized percolate can be removed finally from the respective fermenter 13 and be fed into the sand trap 'white' 12 via the path P2. As long as percolate that is not yet sanitized is removed from the fermenter 13, this will be fed into the sand trap 'black' via the path P1. This percolate from this location enters into the percolate tank and is routed to the percolate outlet 10b and is sanitized in this manner, as described above. Any percolate from the sand trap 'white' 12 that has already been sanitized is made available to the percolate circuit overflowing via the opening or the standing baffle 16.

A corresponding device can be operated as follows, for example: Biomass is placed into the fermenter 13 as substrate. This typically stays in the fermenter 13 for a period between the input of the biomass until its removal, following fermentation of approximately 21 days. During its input, the material temperature corresponds to the ambient conditions, e.g. 10° C. Now the fermentation begins with starting the percolation at a percolate temperature of preferably higher than 50° C., preferably 53° C., wherein the percolate temperature is adjusted such that it reaches said temperature value at the outlet 10b of the percolate tank 10 at any time. For this purpose and for the adjustment of a corresponding temperature value, additional heaters in the percolate tank 10 and/or in one of the two sand traps 11, 12, in the percolate tank 10, particularly in the chambers 1 and 2, can be provided.

During this time, the percolate outflow from the fermenter is always supplied into the sand trap 'black' 11 (arrow P1). During the course of the next days (e.g. up to about the 8th or the 9th day), a thermophilic temperature (preferably >50° C.) of the entire material in the fermenter 13 is obtained at every location in the fermenter and/or the biomass contained therein, by percolation with warm percolate. Consequently, also the material in the fermenter 13 is sanitized approximately after the 10th day, so that the percolate outflow also has a 100% sanitized status. From this time on, the valve 14, 15 of the percolate of the flow is switched so that the percolate outflow enters the sand trap 'white' (arrow P2).

The outflow from the sand trap 'black' 11 enters the percolate tank 10 in the area of the chamber 6 via the inlet 10c. Because of the feed from the not yet completely sanitized contents of the fermenters 13, the temperature at this location will always be less than the temperature (approx. 53° C.) provided for the percolate removal. By heating the chambers (in particular chamber 6 in the heating section 10a) the percolate is preferably heated to 53° C. and is kept at this temperature in the percolate tank 10 along the entire flow path and/or for the entire residence time. Because the percolate flows slowly through the chambers 6 to 1, the percolate is preferably completely sanitized in the vicinity of chambers 3 and 2 after a defined time (e.g. approximately after 5 to 8 days residence time, calculated from the time of entry into chamber 6). At this point, now also the percolate from the outflow 16 of the sand trap 'white' is likewise supplied into the percolate tank 10, which results in that the volumetric flow rate increases after the inlet point.

The two sand traps 11, 12 are preferably always filled 100% up to the height of the overflow weir of the openings 16 and 10c. The water level F10 in the percolate tank 10 must always be lower in relation to this in order to prevent a back flow from the percolate tank 10 back into the sand traps 11, 12 (particularly into the sand trap 'white' 12). A level control is preferably provided for this purpose.

The temperatures mentioned here and particularly the times mentioned are selected as examples and can deviate in practice.

Modifications and substitutions by one of ordinary skill in the art are considered to be within the scope of the present invention, which is not to be limited except by the allowed claims and their legal equivalents.

The invention claimed is:

1. A device for treating percolate recovered from a biomass fermenter which comprises at least one fermenter (13) and a percolate tank (10) for collecting the percolate from the at least one fermenter (13), wherein the percolate tank (10) has a percolate inlet (10c) fluidly coupled to an outlet of the at least one fermenter (13) and configured for receiving percolate from the at least one fermenter (13), and a percolate outlet (10b) fluidly coupled to said percolate inlet (10c) of the percolate tank (10) by means of a flow path (P), characterized in that the flow path (P) in the percolate tank between the percolate inlet (10c) and the percolate outlet (10b) is configured in the form of a non-direct, extended flow path (P) selected from the group of flow paths consisting of a meander path, a spiral path and a helical path, said non-direct extended flow path (P) having a predetermined length and configured for providing an extended flow path (P) for said percolate received from the at least one fermenter (13), for providing a sufficiently long dwell time for the percolate at a thermophilic adapted temperature, the predetermined length of the flow path of the percolate and the temperature of the percolate along the extended flow path between the percolate inlet (10c) and the percolate outlet (10b) configured such that only sanitized percolate is drawn off at the percolate outlet (10b).

2. The device according to claim 1, characterized in that the percolate tank (10) is arranged below the at least one fermenter (13).

3. The device according to claim 1, characterized in that a plurality of fermenters (13) are provided of which at least one is designed for an at least temporary thermophilic operation.

4. The device according to claim 3, characterized in that between the at least one fermenter (13) and the percolate tank

(10) at least one apparatus (11, 12) is connected and configured for cleaning the percolate.

5. The device according to claim 4, characterized in that at least two apparatuses (11) and (12) are provided for cleaning the percolate, wherein fermenters (13) and the apparatuses (11) and (12) can be connected such that sterilized percolate coming from a fermenter (13) is supplied into the one apparatus (12) and that non-sanitized percolate coming from a fermenter (13) is respectively provided into the other apparatus (11).

6. The device according to claim 1, characterized in that at least one heating section (10a) is provided in the percolate tank (10) downstream of the percolate inlet (10c), in which the percolate that is entering the percolate tank (10) can be heated to a specified temperature.

7. The device according to claim 5, characterized in that at least one of the apparatuses (11) and (12) is a sand trap.

8. The device according to claim 5, characterized in that in the percolate tank (10) and/or in one and/or in both of the apparatuses (11, 12) a heater is provided for cleaning the percolate which can be operated so that a specified minimum temperature of the percolate is adjusted.

\* \* \* \* \*